United States Patent [19]

Lehmann

[11] Patent Number: 4,860,749
[45] Date of Patent: Aug. 29, 1989

[54] TACHYCARDIA DETECTION FOR AUTOMATIC IMPLANTABLE CARDIOVERTER/DEFIBRILLATOR WITH ATRIAL AND VENTRICULAR SENSING CAPABILITY

[75] Inventor: Michael H. Lehmann, West Bloomfield, Mich.

[73] Assignee: Wayne State University, Detroit, Mich.

[21] Appl. No.: 141,280

[22] Filed: Jan. 6, 1988

[51] Int. Cl.⁴ .................... A61N 1/00; H05G 00/00
[52] U.S. Cl. ............................................. 128/419 PG
[58] Field of Search ......... 128/419 D, 419 PG, 419 P

[56] References Cited

U.S. PATENT DOCUMENTS

| | | | |
|---|---|---|---|
| 4,421,116 | 12/1983 | Markowitz | 128/419 PG |
| 4,577,634 | 3/1986 | Gessman | 128/419 PG |
| 4,624,260 | 11/1986 | Baker, Jr. et al. | 128/419 PG |
| 4,712,555 | 12/1987 | Thornander et al. | 128/419 PG |

Primary Examiner—Francis Jaworski
Assistant Examiner—George Manuel
Attorney, Agent, or Firm—Reising, Ethington, Barnard Perry & Milton

[57] ABSTRACT

An automatic tachycardia detection assembly to be implanted in a person for stimulating the heart upon detection of abnormal tachycardias. The assembly includes an atrial sensor (16) and ventricular sensor (18) for sensing activity within the atria and ventricles of the heart, respectively. Also included is an electrical stimulator or cardioverter/defibrillator (20, 22) for therapeutically stimulating the heart upon detection of abnormal tachycardias. The assembly (10) includes a housing (12) enclosing a control circuit (14) to be implanted within a person responsive to the sensors (16, 18) controlling the cardioverter/defibrillator (20, 22). The control circuit (14) distinguishes sinus tachycardia from ventricular tachycardia having 1:1 VA conduction by comparing the measured tachycardia AV interval to a predetermined sinus AV interval.

12 Claims, 3 Drawing Sheets

TACHYCARDIA DETECTION FOR AUTOMATIC IMPLANTABLE CARDIOVERTER/DEFIBRILLATOR WITH ATRIAL AND VENTRICULAR SENSING CAPABILITY

TECHNICAL FIELD

This invention relates to automatic implantable devices to detect and differentiate between tachycardias (rapid heart rhythms) so as to therapeutically stimulate the heart in response thereto, and more specifically to distinguish sinus tachycardia (physiologic) from ventricular tachycardia (pathologic).

BACKGROUND OF THE INVENTION

Early automatic tachycardia detection systems have relied solely on heart rate for the diagnosis of pathological tachycardia which is often confused with sinus tachycardia. The basis of these systems was that any rate exceeding a predetermined value resulted in a tachycardia termination response. This predetermined value is generally in the vicinity of 150 beats/min (400 ms cycle length). Recent automatic implantable cardioverter/defibrillators may improve discrimination between tachycardias, but still frequently mistake sinus or other supraventricular tachycardias for ventricular tachycardia, resulting in inappropriate cardiac electrical stimulation.

As stated in "Tachycardia Recognition by Implantable Electronic Devices" by Camm, Davies, and Ward, PACE 10:1175, 1987, physiological tachycardia (i.e., sinus tachycardia) may still be confused with pathological tachycardia, especially when abnormal tachycardia arises during sinus tachycardia or sinus tachycardia is present after successful termination of pathological tachycardia. The Article outlines several methods attempting to advance tachycardia recognition, but none can perfectly detect the onset of pathological tachycardia. Such methods include heart rate change algorithm, probability density function, etc.

Future devices may incorporate atrial sensing as well as the well known ventricular sensing. As a result, ventricular tachycardia with AV dissociation or a non-1:1 VA response will be easily distinguished from both atrial tachyarrhythmias associated with second degree AV block and sinus tachycardia. A problem which arises is to accurately differentiate cases of ventricular tachycardia with 1:1 VA conduction from sinus tachycardia which also has a 1:1 A:V relationship. More precise methods of tachycardia detection are needed to handle this problem.

SUMMARY OF THE INVENTION AND ADVANTAGES

The invention is an automatic tachycardia detection assembly and method of performing the same. The assembly is to be implanted in a person for therapeutically stimulating the heart upon detection of abnormal tachycardias and comprises atrial sensing means for sensing the electrophysiological activity and cycle length of successive beats within the atrium and ventricular sensing means for sensing the electrophysiological activity and the cycle length of successive beats within the ventricle. Control means is responsive to the atrial sensing means and the ventricular sensing means for determining the atrium to ventricle time interval (AV interval) detecting ventricular tachycardia and actuating the stimulation means and for distinguishing sinus tachycardia when the ventricular cycle length is equal to the atrial cycle length and the AV interval during tachycardia is less than or equal to a predetermined AV interval representing the sinus AV interval to prevent unnecessary stimulation of the heart.

The advantages of the invention include the use of both the atrial sensor and the ventricular sensor to determine the tachycardia AV interval so that it can be compared to the sinus AV interval in order to determine whether the tachycardia is physiologic (sinus) or pathologic (likely to be ventricular tachycardia).

DESCRIPTION OF THE DRAWINGS

Other advantages of the present invention will be readily appreciated as the same becomes better understood by reference to the following detailed description when considered in connection with the accompanying drawings wherein.

DESCRIPTION OF THE PREFERRED EMBODIMENT

Figure 1:
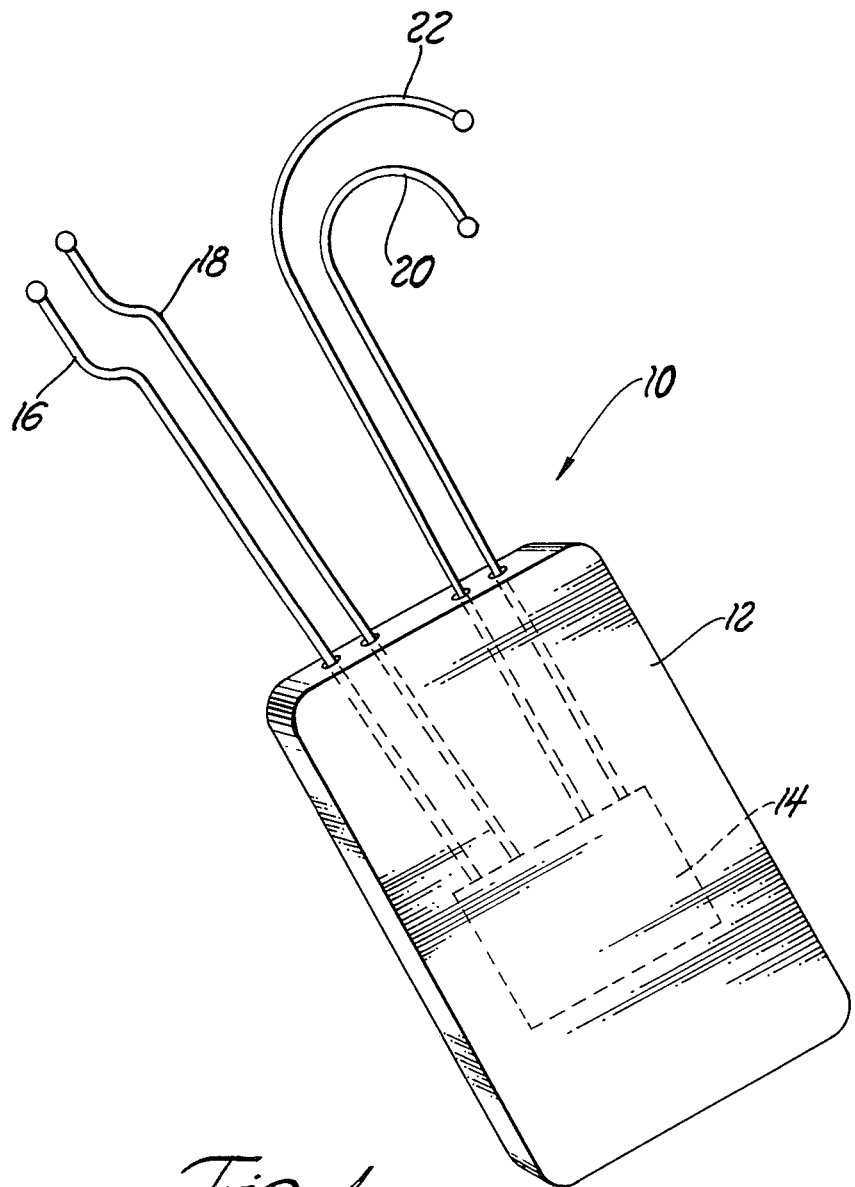
FIG. 1 is a perspective view of the subject invention.

An automatic implantable cardioverter defibrillator assembly with high capability for differentiating sinus and other supraventricular tachycardias from ventricular tachycardia using combined atrial and ventricular sensing is generally shown in FIG. 1 at 10.

The assembly 10 includes a control housing 12 to be implanted within a person. The control housing 12 may be any suitable implantable housing as well known in the art. Control means 14 is located within the control housing 12 for detecting various tachycardias.

The assembly 10 also includes atrial sensing means 16 for sensing the electrophysiological activity or beats within an atrium of the heart. Ventricle sensing means 18 senses the electrophysiological activity or beats within a ventricle of the heart. The atrial 16 and ventricular 18 sensors maybe termed input means and are electrodes as well known in the art. The atrial sensor 16 is preferably placed at the high right atrium and the ventricular sensor 18 is preferably placed at the right ventricular apex. The control means 14 is responsive to the atrial 16 and ventricular 18 sensing means for determining the occurrence of ventricular tachycardia. The control means 14 receives electrocardiographic signals from both sensors 16, 18 and determines the cycle length of the electrical activity in each respective chamber. The cycle length is the time interval between successive beats of the heart. The control means 14 also determines the AV (typically the high right atrium to right ventricular apex) interval by measuring the time difference between a sensed beat from the atrial sensing means 16 and a sensed beat from the ventricular sensing means 18.

The assembly 10 includes stimulation means 20, 22 responsive to the control means 14 for electrically stimulating the heart upon the occurrence of certain tachycardia conditions as discussed subsequently. The stimulating means 20, 22 may be termed output means and may include electrodes connected to different areas of the heart for cardioversion/overdrive pacing/defibrillation, etc., or any other known method of controlling the heart rate.

The control means 14 may include a processing semiconductor chip, such as a microprocessor, for processing information received from the sensing means 16, 18 and for operation of the stimulating means 20, 22. Included within the chip 14 is an algorithm for determining when the heart is to be stimulated, as will be described subsequently. It is to be understood that the algorithm method may be implemented by various circuit combinations and is not to be limited to a semiconductor chip. The stimulating means 20 may be implemented by any well known methods to control the heart rate.

As background, there is a ventricular cycle length below which clinically significant (potentially symptom producing or life threatening) ventricular tachycardia may occur which requires intervention. Conversely, there is a ventricular rate above which clinically significant ventricular tachycardia may occur. This cycle length value is called the threshold value and the rate called the threshold rate for purposes of this disclosure. Ventricular tachycardia with AV dissociation or a non-1:1 VA (ventriculoatrial) response will be easily distinguished from both atrial tachyarrhythmias associated with second degree AV block and sinus tachycardia. There is also a ventricular cycle length over which ventricular tachycardia associated with 1:1 VA conduction will not be mistaken for sinus tachycardia, and conversely a ventricular rate under which ventricular tachycardia will not be mistaken. This cycle length value is called the crossover value and the rate value will be referred to as the crossover rate for the purposes of this disclosure as will be subsequently described. The converse is true when dealing with rates (beats/minute) instead of cycle lengths (milliseconds).

Tests have been accomplished to determine clinically appropriate threshold value and crossover value. Traditionally, data has indicated that abnormal tachycardias may occur at rates over 150 beats/min or cycle lengths less than 400 msec. It may be possible to lower the threshold rate (beats/min) or raise the threshold value (msec) to attempt ventricular overdrive conversion, etc. of a relatively slower ventricular tachycardias.

To determine the crossover value, the data has indicated that for tachycardia rates up to approximately 170 beats/minute, ventricular tachycardia can be successfully differentiated from sinus tachycardia in most patients with good retrograde conduction. Ventricular tachycardia with 1:1 VA conduction at rates below the crossover rate would be accurately differentiated from sinus tachycardia. At rates above this crossover rate, or cycle lengths below the crossover value, the AV relationship prevailing during sinus tachycardia would be mimicked. Accordingly, the assembly 10 needs to be programmed to presume a diagnosis of ventricular tachycardia for tachycardias at rates above the crossover rate (below the crossover value) up to the point at which 1:1 VA conduction during the tachycardia fails. From that rate upwards, AV dissociation during ventricular tachycardia would be apparent to the assembly 10. The crossover value needs to be determined in each patient prior to or at the time of implantation via the actual right atrium and ventrical trasvenous or epicardial electrodes 16, 18 which are utilized by the assembly 10. This crossover value may be determined by the ventricular cycle length at which the AV interval during 1:1 VA conduction equals the baseline (sinus) AV interval or, ideally, the AV interval during sinus tachycardia (to a rate at least equal to the rate cutoff, typically 150 beats/min). These reference AV intervals are measured by the sensors 16, 18.

One of the major advantages of the invention is the handling of tachycardia rates above the crossover value. The AV interval stays the same or usually shortens during sinus tachycardia, owing to the dual effects on both the sinus and AV nodes which occur during the vagal withdrawal and heightened sympathetic tone that accompany the physiologic response which constitutes sinus tachycardia. The basis of the algorithm is that in persons with 1:1 VA conduction to cycle lengths less than the crossover value (greater than the threshold rate of 150 beats/minute), a non-sinus tachycardia criterion is proposed in which the AV interval during tachycardia must be greater than the AV interval during normal sinus rhythm (or during physiologic sinus tachycardia), termed the sinus AV interval. Thus, the non-sinus criteria can be utilized for tachycardia cycle lengths between the crossover and threshold values.

The criterion can be assessed by AV interval tracking during the tachycardia. The sinus AV interval needs to be determined at implantation or prior by using the atrial 16 and ventricular 18 sensors. The sinus AV interval is a value used in the algorithm to be compared to the tachycardia AV interval. The sinus AV interval is measured with the patient resting, or ideally during the infusion of adrenaline or when the patient is exercising.

If ventricular tachycardia with 1:1 VA conduction appears but fails to satisfy the non-sinus tachycardia criterion, then it would be safe for the device to assume that a nonphysiologic 1:1 A:V tachycardia is occurring. Such a tachycardia could also represent AV nodal reentry, AV reciprocating tachycardia, or even an atrial tachycardia with 1:1 conduction, all of which are relatively uncommon, however. Therefore, a diagnosis of ventricular tachycardia would be overwhelmingly likely to be correct when the non-sinus tachycardia criterion is met.

Figure 2A:
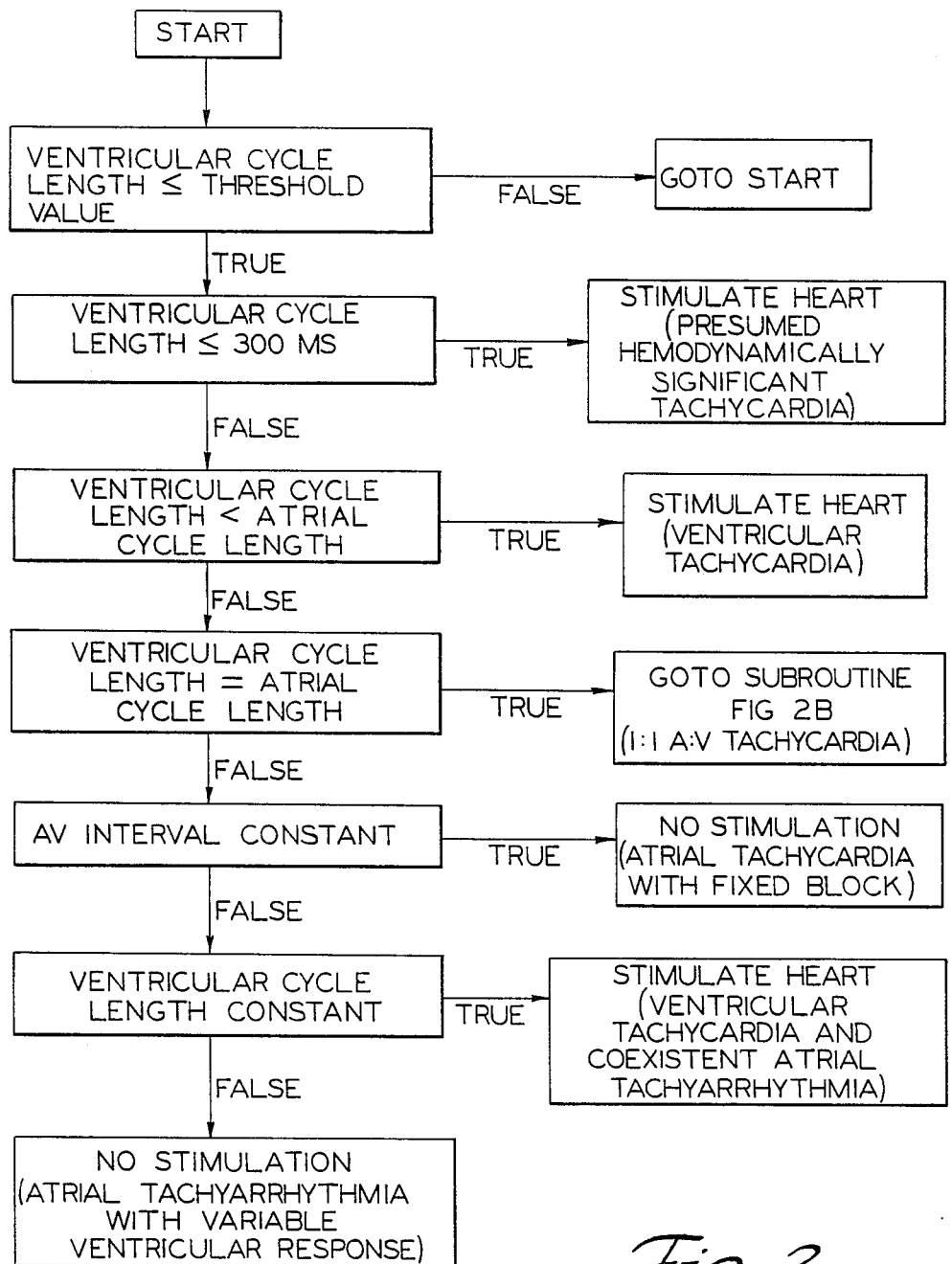
FIG. 2a is a flow chart of the main algorithm of the control means of the subject invention.
Figure 2B:
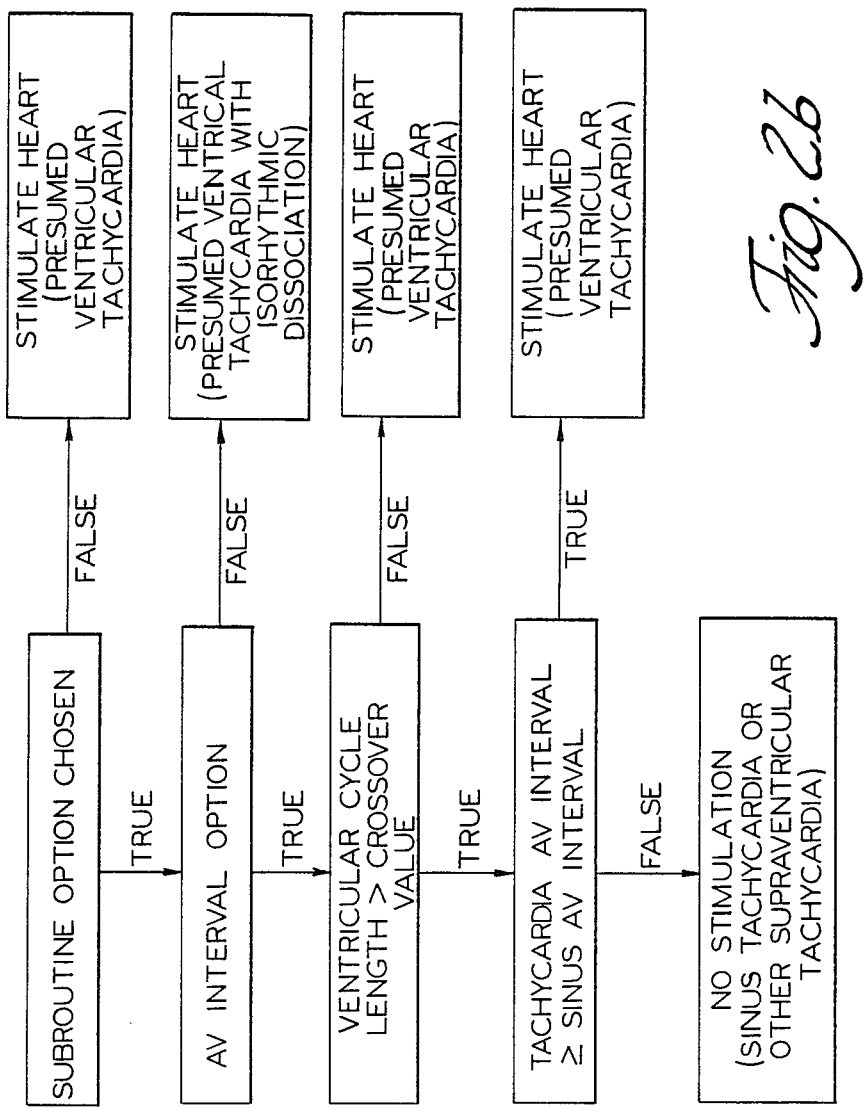
FIG. 2b is a flow chart of the subroutine of the main algorithm of the subject invention.

Shown in FIG. 2 is the algorithm which may be utilized by an automatic implantable cardioverter/defibrillator assembly 10 with atrial 16 and ventricular 18 sensing capability to accurately differentiate ventricular tachycardia from most cases of sinus tachycardia and supraventricular tachycardia, especially when the latter is associated with functional second degree AV block. FIG. 2a incorporates well known electrocardiagraphic concepts, but also takes into account the unusual occurrence of ventricular tachycardia that is below the threshold value but which occurs during a coexistent (faster) atrial tachyarrhythmia. This phenomenon is able to be recognized because both the ventricular and atrial cycle lengths are compared. FIG. 2b is for the condition of 1:1 A:V tachycardia discrimination, or when the ventricular cycle length is equal to the atrial cycle length. If not for this portion of the algorithm, sinus tachycardia might erroneously be identified as ventricular tachycardia at cycle lengths below the threshold value for the assembly 10, resulting in inappropriate cardiac stimulation by the stimulation means 20, 22. It should be stressed that while the subroutine FIG. 2b could mistakenly identify some supraventricular tachycardias with 1:1 A:V relationship as ventricular tachycardia, these situations are relatively uncommon and the underlying tachyarrhythmias can often be characterized during baseline electro-physiology studies and brought under control with antiarrhythmic agents. Most importantly, the assembly must err on the side of oversensitivity so as never to permit an actual case of ventricular tachycardia/ventricular fibrillation to go undetected.

As illustrated in FIG. 2a, the algorithm is entered upon the first condition that the sensed ventricular cycle length is less than or equal to the threshold value. As previously discussed, this threshold value may be 400 msec. The second step within the algorithm is to test if the ventricular cycle length is less than or equal to a predetermined value representing the value below which hemodynamically significant tachycardia is presumed. This value has been tested to be in the vicinity of 300 ms. If this condition is true, it is presumed that a hemodynamically significant tachycardia condition exists and the heart is stimulated. If this condition is false, a third condition is tested. The third condition tested is whether the ventricular cycle length is less than the atrial cycle length. If true, a condition of ventricular tachycardia is determined and the heart is stimulated. If false, a fourth step is tested. The fourth step is to test whether the ventricular cycle length is equal to the atrial cycle length. If true, 1:1 A:V tachycardia is determined and the subroutine of FIG. 2b is branched to, which will be described subsequently. If the fourth test is determined false, then a fifth condition is tested. The fifth condition tests whether the AV interval is constant. If true, a condition of atrial tachytarrhythmia with fixed block is determined and the heart is not stimulated. If false, a sixth condition is tested. The sixth condition tests whether the ventricular cycle length is constant. If true, then a condition of ventricular tachycardia and coexistent atrial tachyarrhythmia is determined and the heart is stimulated. If false, then a condition of atrial tachyarrhythmia with variable ventricular response is presumed and the heart is not stimulated.

The subroutine of FIG. 2b is entered upon the condition that the ventricular cycle length and the atrial cycle length are equal indicating 1:1 A:V tachycardia. Within the subroutine, the first step is to test whether the subroutine option has been chosen. In some patients, it may be desirable to stimulate the heart upon the 1:1 AV tachycardia detection, and this may be programmed to dissallow patients from continuing in the subroutine. If the subroutine is chosen in the first step, the second step is to test whether the AV interval is constant. If false, then a condition of ventricular tachycardia is presumed with isorhythmic dissociation and the heart is stimulated. If true, a third step is entered which tests whether the ventricular cycle length is greater than the crossover value. If false, a condition of ventricular tachycardia is presumed and the heart is stimulated. If true, a forth test is entered which tests whether the tachycardia AV interval is greater than or equal to the sinus AV interval. If true, a condition of ventricular tachycardia is presumed and the heart is stimulated. If false, conditions of sinus tachycardia or other supraventricular tachycardias are presumed and the heart is not stimulated.

When the algorithm determines whether the heart is stimulated or not stimulated, the control means 14 is then reset and the algorithm begins again at START testing the first condition of the main algorithm FIG. 2a. This occurs whether in the main algorithm or the subroutine algorithm.

The threshold value add crossover value will need to be modified over time as various changes occur in the patients, underlying condition and medical regimen. This necessitates that the assembly 10 be capable of supporting noninvasively-contolled ventricular pacing with beat-to-beat telemetric transmission of actual high right atrial to ventricular stimulus intervals. Serial noninvasive measurement of the sinus AV interval through the atrium 16 and ventrical 18 electrodes would thus also be possible. Without such capability, temporary pacemaker insertion would be necessary each time physiologic calibrations have to be made in the algorithm.

It is to be understood that the algorithm FIG. 2a and 2b may include additional tachycardia criteria or changes in the tachycardia criteria.

Studies have been accomplished using the subject assembly 10. A 1:1 A:V relationship was lacking in 25 of 30 patients capable of sustained monomorphic ventricular tachycardias to rates above 150 beats/min inducible in 25 consecutive unmedicated patients undergoing electrophysiologic studies. All of these ventricular tachycardias were correctly identified in the third step of the main algorithm (test: ventricular cycle length atrial cycle length). In four patients who had 1:1 VA conduction during ventricular tachycardia (rates 175 to 230 beats/min), the VA conduction was not 1:1 initially for 14–21 seconds during three of the tachycardias. This lag time in these cases could be expected to provide the device with sufficient time to make the appropriate diagnosis using the algorithm of the assembly 10. The remaining case was correctly identified in the sixth step of the main algorithm (test: ventricular cycle length constant). Overall, 29 of the 30 ventricular tachycardias were correctly identified using the main algorithm FIG. 2a. Of the four patients who either initially had or subsequently developed 1:1 VA conduction during the tachycardia, and including the single missed ventricular tachycardia of the main algorithm FIG. 2a, the subroutine FIG. 2b was applied. In all cases the non-sinus tachycardia criterion was satisfied indicating that tachycardia termination by the assembly 10 would be indicated and appropriate.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. An automatic tachycardia detection and cardiac stimulating assembly adapted to be implanted in a person for stimulating the heart of the person upon detection of an abnormal tachycardia, said assembly comprising; atrial sensing means (16) for sensing electrophysiological activity within an atrium of said heart ventricular sensing means (18) for sensing electrophysiological activity within a ventricle stimulation means (20, 22) adapted to be connected to the heart for electrically and therapeutically stimulating the heart, and control (14) operatively connected to said atrial sensing means and said ventricular sensing means and said stimulating means and responsive to said sensed activity from said atrial sensing means (16) and said ventricular sensing means (18) for (a) determining cycle length of atrial activity and cycle length of ventricular activity (b) for determining the atrium to ventricle time interval (AV interval) (c) detecting ventricular tachycardia from said determined ventricular cycle length and actuating said stimulating means (20, 22) when ventricular tachycardia is detected, and (d) for distinguishing sinus tachycardia when the determined ventricular cycle length is equal to the determined atrial cycle length and the AV interval during tachycardia is less than or equal to a predetermined AV interval representing a normal sinus AV conduction interval and preventing activation of said stimulating means, thereby to prevent unnecessary stimulation of the heart.

2. A method of detecting tachycardia in a heart and stimulating the heart in response to the detecting the method including the steps of; sensing electrophysiological activity within an atrium, sensing electrophysiological activity within a ventricle, determining atrial cycle length of the activity within the atrium and ventricular cycle length of the activity within the ventricle, determining ventricular tachycardia from said cycle lengths and stimulating the heart in response thereto while preventing unnecessary stimulation of the heart when the sensed ventricular cycle length is equal to the sensed atrial cycle length and sinus tachycardia detected by the atrium to ventricle time interval (AV interval) length of a beat during tachycardia is less than or equal to a predetermined AV interval representing normal sinus rhythm.

3. A method as set forth in claim 2 further including detecting when the sensed ventrical cycle length is less than a threshold value representing the value below which tachycardia can occur and preventing stimulating when above the threshold value.

4. A method as set forth in claim 3 further including stimulating the heart when the ventricular cycle length is less than or equal to a predetermined value representing the value below which hemodynamically significant tachycardia is presumed.

5. A method as set forth in claim 4 further including stimulating the heart when the ventricular cycle length is less than the atrial cycle length and the ventrical cycle length is less than or equal to the predetermined value.

6. A method as set forth in claim 5 further including stimulating the heart when the ventricular cycle length equals the atrial cycle length and the AV interval is not constant.

7. A method as set forth in claim 6 further including stimulating the heart when the ventricular cycle length equals the atrial cycle length and the ventricular cycle length is less than or equal to a crossover value representing a value below which abnormal tachycardia may occur having a 1:1 VA conduction.

8. A method as set forth in claim 7 further including stimulating the heart when the ventricular cycle length equals the atrial cycle length and exceeds said crossover value and the tachycardia AV interval is greater than or equal to the sinus AV interval, and preventing firing when tachycardia AV interval is less than the sinus AV interval.

9. A method as set forth in claim 8 further including stimulating the heart when the ventricular cycle length is not less than or equal to the atrial cycle length and the AV interval is not constant and the ventricular cycle length is constant, and preventing stimulation of the heart when the AV interval is constant or when the ventricular cycle length is not constant.

10. An automatic tachycardia detection and cardiac stimulating assembly adapted to be implanted in a person for stimulating the heart of the person upon detection of an abnormal tachycardia, said assembly comprising; atrial sensing means (16) for sensing electrophysiological activity within the atrium of said heart ventricular sensing means (18) for sensing electrophysiological activity within the ventricle, stimulation means (20, 22) for stimulating the heart to control the heart rate, and control means (14) operatively connected to said atrial sensing means and said ventricular sensing means and said stimulation means and responsive to said sensed activity from said atrial sensing means (16) and said ventricular sensing means (18) for determining ventricular cycle length and atrium to ventricular time interval (AV interval), for detecting ventricular tachycardia from said ventricular cycle length and said AV time interval and actuating said stimulation means (20, 22) when tachycardia is detected.

11. A control mechanism for an automatic tachycardia detector assembly to be implanted in a person for stimulating the heart upon detection of abnormal tachycardias including an atrial sensor (16) and ventricular sensor (18) for sensing electrophysiological activity and cycle length of successive beats in the heart and a stimulator (20, 22) for electrically and therapeutically stimulating the heart, said control mechanism (14) including input means for being responsive to the atrial sensor (16) and the ventricular sensor (18) for determining the atrium to ventricular time interval (AV interval) detecting ventricular tachycardia output means for and actuating the stimulator (20, 22) and for distinguishing sinus tachycardia when the ventricular cycle length is equal to the atrial cycle length and the AV interval during tachycardia is less than or equal to a predetermined AV interval normal sinus AV interval to prevent unnecessary stimulation of the heart.

12. A method of detecting ventricular tachycardia and stimulating a heart the method including the steps of; sensing electrophysiological activity within an atrium measuring the atrial cycle length sensing electrophysiological activity within a ventricle, measuring the ventricular cycle length measuring the atrial to ventricular conduction time interval (AV interval) representative of the time between sensed electrophysiological activity within the atrium and sensed electrophysiological activity ventrical, and comparing the measured AV interval and the ventricle cycle length and the atrial cycle length for determining whether tachycardia is present and stimulating the heart when tachycardia is present.

* * * * *